United States Patent
Nitta (10) Patent No.: US 10,022,515 B2
(45) Date of Patent: Jul. 17, 2018

(54) EXHALATION VALVE AND RESPIRATORY ASSISTANCE DEVICE

(75) Inventor: Kazufuku Nitta, Kawaguchi (JP)

(73) Assignee: METRAN CO., LTD., Kawaguchi-shi, Saitama (JP)

(*) Notice: Subject to any disclaimer, the term of this patent is extended or adjusted under 35 U.S.C. 154(b) by 629 days.

(21) Appl. No.: 14/344,189

(22) PCT Filed: Sep. 12, 2012

(86) PCT No.: PCT/JP2012/073333
§ 371 (c)(1),
(2), (4) Date: Mar. 11, 2014

(87) PCT Pub. No.: WO2013/039104
PCT Pub. Date: Mar. 21, 2013

(65) Prior Publication Data
US 2015/0040904 A1    Feb. 12, 2015

(30) Foreign Application Priority Data
Sep. 12, 2011 (JP) ................. 2011-198258

(51) Int. Cl.
*A61M 16/20* (2006.01)
*A61M 16/00* (2006.01)

(52) U.S. Cl.
CPC .......... *A61M 16/205* (2014.02); *A61M 16/20* (2013.01); *A61M 16/201* (2014.02);
(Continued)

(58) Field of Classification Search
CPC .... A61M 16/00; A61M 16/20; A61M 16/201; A61M 16/205; A61M 16/203; A61M 16/202; A61M 16/206
See application file for complete search history.

(56) References Cited

U.S. PATENT DOCUMENTS

| 4,241,756 A | 12/1980 | Bennett et al. |
| 5,315,989 A | 5/1994 | Tobia |

(Continued)

FOREIGN PATENT DOCUMENTS

| DE | 195 43 248 A1 | 5/1996 |
| JP | 4-200478 A | 7/1992 |

(Continued)

OTHER PUBLICATIONS

European Search Report issued in Appln. No. EP 12831313.7 dated Dec. 5, 2014 (5 pages).

(Continued)

*Primary Examiner* — Justine Yu
*Assistant Examiner* — Colin W Stuart
(74) *Attorney, Agent, or Firm* — Flynn, Thiel, Boutell & Tanis, P.C.

(57) ABSTRACT

Exhalation valve including a diaphragm for opening and closing an outlet of an exhalation flow path for guiding exhaled air to the outside air, a back chamber provided opposite the exhalation flow path in the diaphragm and forming a space together with the diaphragm, and a pump unit fixed to the circumference of the back chamber for adjusting the air pressure inside the back chamber by feeding and discharging of air to and from the back chamber. The diaphragm closes the outlet of the exhalation flow path when the air pressure inside the exhalation flow path is lower than the air pressure inside the back chamber, and opens the outlet of the exhalation flow path when the air pressure inside the exhalation flow path is higher than the air pressure inside the back chamber.

4 Claims, 11 Drawing Sheets

(52) U.S. Cl.
CPC ........ *A61M 16/202* (2014.02); *A61M 16/203* (2014.02); *A61M 16/206* (2014.02); *A61M 16/0003* (2014.02); *A61M 16/0066* (2013.01); *A61M 16/0069* (2014.02); *A61M 16/024* (2017.08); *A61M 2016/0027* (2013.01); *A61M 2016/0039* (2013.01); *A61M 2205/0244* (2013.01); *A61M 2205/3337* (2013.01); *A61M 2205/50* (2013.01)

(56) References Cited

U.S. PATENT DOCUMENTS

| | | | |
|---|---|---|---|
| 5,765,558 | A | 6/1998 | Psaros et al. |
| 7,823,588 | B2 * | 11/2010 | Hansen ................. A61M 16/00 128/204.18 |
| 2003/0172931 | A1 * | 9/2003 | Kerechanin, II ...... A61M 16/00 128/204.18 |
| 2006/0096596 | A1 | 5/2006 | Occhialini et al. |
| 2010/0139660 | A1 * | 6/2010 | Adahan ............. A61M 16/0057 128/205.24 |
| 2010/0186744 | A1 | 7/2010 | Andrieux |
| 2013/0167843 | A1 * | 7/2013 | Kimm ................. F16K 31/1266 128/205.24 |

FOREIGN PATENT DOCUMENTS

| | | |
|---|---|---|
| JP | 4-215766 A | 8/1992 |
| JP | 5-245204 A | 9/1993 |
| JP | 7-246240 A | 9/1995 |
| JP | 9-108353 A | 4/1997 |
| JP | 2002-136598 A | 5/2002 |
| JP | 2006-130320 A | 5/2006 |
| JP | 2010-540119 A | 12/2010 |
| WO | WO 2009/006932 A1 | 1/2009 |
| WO | WO 2009/042974 A1 | 4/2009 |

OTHER PUBLICATIONS

International Search Report issued in PCT/JP2012/073333 with English Translation dated Oct. 16, 2012 (4 pages).

* cited by examiner

EXHALATION VALVE AND RESPIRATORY ASSISTANCE DEVICE

TECHNICAL FIELD

The present invention relates to an exhalation valve using a diaphragm and a respiratory assistance device using the exhalation valve.

BACKGROUND ART

In medical practice, respiratory assistance devices, such as an artificial ventilator, are used. As the respiratory assistance device, various methods are adopted including such methods as a controlled ventilation (Controlled Ventilation) method that is used for patients unable to breathe spontaneously (patients under general anesthesia, cardiopulmonary resuscitation, or in a critical condition), an assisted ventilation (Assisted Ventilation) method that generates a positive pressure (positive pressure) in an air passage in accordance with the spontaneous breathing of a patient, a partial assisted ventilation (Assist/Control) method that combines the assisted ventilation and the controlled ventilation, and a high frequency oscillation ventilation (high frequency oscillation) method that realizes an extremely low amount of one-time ventilation of 1 to 2 ml/kg by vibrating gas supplied by the air passage at a frequency of 5 to 40 Hz.

Each of these respiratory assistance devices requires a pump unit that generates the positive pressure in the air passage and an exhalation valve that discharges exhaled air to the outside air while maintaining the positive pressure.

The pump unit uses a relatively large device as a power source, such as a blower that transports a gas by rotating a fan and a cylinder pump that transports a gas by causing a piston to be reciprocated. Therefore, in conventional respiratory assistance devices, a box-shaped casing accommodating the pump unit is used while being installed beside a user.

There are some exhalation valves with a structure that is simplified by using a diaphragm (for example, see Japanese Patent Application Laid-Open No. Hei. 05-245204). The diaphragm is arranged so as to close an outlet of a pipe line that guides the exhaled air, and opens the pipe line by deforming in the direction moving farther away from the outlet. On the opposite side to the pipe line in the diaphragm, a back chamber to and from which the pump unit feeds and discharges air is provided. More specifically, the diaphragm is arranged so as to separate a space inside the pipe line from a space inside the back chamber and functions using a difference in air pressures between those spaces.

More specifically, when the air pressure inside the pipe line is lower than the air pressure inside the back chamber, the diaphragm adheres to and seals the outlet of the pipe line. On the other hand, when the air pressure inside the pipe line is higher than the air pressure inside the back chamber, the diaphragm deforms to the side of the back chamber and opens the pipe line to release the exhaled air to the outside air. According to the exhalation valve, even when a patient coughs or sneezes, since the diaphragm instantaneously responds thereto and the exhaled air is released to the outside air, the air pressure inside the pipe line does not increase excessively, and consequently, it is possible to inhibit placing an additional burden on the patient.

SUMMARY OF INVENTION

Technical Problem

From the pump unit installed beside a user, there is a pathway leading to the back chamber. Therefore, some response time is required before power from the pump unit starts acting on the back chamber. It is desirable to shorten the response time and be able to accurately control an exhalation valve in medical practice in which human lives are at stake.

The present invention has been made in order to solve the above-described problems, and an object thereof is to provide an exhalation valve that can be accurately controlled and a respiratory assistance device that includes the exhalation valve.

Solution to Problem

The above-described object is achieved by means described below based on extensive research made by the present inventor.

More specifically, the means for achieving the above-described object is an exhalation valve including: a diaphragm for opening and closing an outlet of an exhalation flow path for guiding exhaled air to the outside air; a back chamber that is provided on the opposite side of the exhalation flow path in the diaphragm and forms a space together with the diaphragm; a pump unit that is provided to the circumference of the back chamber, for adjusting the air pressure inside the back chamber by performing feeding and discharging of air to and from the back chamber; and a control unit for controlling the operation of the pump unit. The exhalation valve with the above configuration is characterized in that the diaphragm uses a difference between the air pressure inside the exhalation flow path and the air pressure inside the back chamber to close the outlet when the air pressure inside the exhalation flow path is lower than the air pressure inside the back chamber, and to open the outlet when the air pressure inside the exhalation flow path is higher than the air pressure inside the back chamber.

In the above-described invention, the exhalation valve that achieves the above-described object is preferably characterized by including a first air pressure gauge for measuring the air pressure inside the exhalation flow path to output the measurement result to the control unit and a second air pressure gauge for measuring the air pressure inside the back chamber to output the measurement result to the control unit, wherein the control unit controls the operation of the pump unit on the basis of the measurement results of the first and second air pressure gauges to cause the difference between the air pressure inside the exhalation flow path and the air pressure inside the back chamber to become substantially zero.

In the above-described invention, the pump unit of the exhalation valve that achieves the above-described object is preferably characterized by including an air feeding micro pump for feeding air to the back chamber and an air discharging micro pump for discharging air from the back chamber.

In the above-described invention, the air feeding micro pump of the exhalation valve that achieves the above-described object is preferably characterized by including an air feeding inlet that takes in a gas from outside the back chamber and an air feeding outlet that is directly connected to the back chamber and discharges the gas taken in from the air feeding inlet into the back chamber, and the air discharging micro pump is preferably characterized by including an air discharging inlet that is directly connected to the back chamber and directly takes in the gas from inside the back chamber and an air discharging outlet that discharges the gas taken in from the air discharging inlet to outside the back chamber.

In the above-described invention, the control unit of the exhalation valve that achieves the above-described object is preferably characterized by controlling the air pressure inside the back chamber by causing both the air feeding micro pump and the air discharging micro pump to operate simultaneously and then causing one of the air feeding micro pump and the air discharging micro pump to stop operating.

In the above-described invention, the pump unit of the exhalation valve that achieves the above-described object is preferably characterized by including a micro pump that has an inlet that takes in a gas and an outlet that discharges the gas taken in from the inlet, one of the inlet and the outlet being selectively connected to the back chamber, and a switching mechanism for causing feeding and discharging of the air to and from the back chamber to be selectively performed by switching connection relationships of the inlet and the outlet with the back chamber.

In the above-described invention, the switching mechanism of the exhalation valve that achieves the above-described object is preferably characterized by switching a position of the micro pump between an air discharging position, in which the inlet is directly connected to the back chamber and the micro pump discharges air from the back chamber, and an air feeding position, in which the outlet is directly connected to the back chamber and the micro pump feeds air to the back chamber.

In the above-described invention, the means for achieving the above-described object is a respiratory assistance device that is characterized by including: an inhalation flow path for guiding a gas from a supply source, which is different from the pump unit, to a living organism, the gas becoming exhaled air; an exhalation flow path for guiding the exhaled air of the living organism to the outside air; and the exhalation valve, according to any one of the above-described inventions, that adjusts the air pressure inside the exhalation flow path by releasing the gas inside the exhalation flow path to the outside air.

Advantageous Effects of Invention

According to the present invention, it is possible to achieve an excellent effect in which an exhalation valve can be accurately controlled.

BRIEF DESCRIPTION OF DRAWINGS

FIG. 3 (A) is a cross-sectional view illustrating an example of a structure of a micro pump used in a pump unit and FIG. 3 (B) is a graph showing a pressure-flow rate line of the micro pump.

DESCRIPTION OF EMBODIMENTS

Examples of embodiments of the present invention will be described below with reference to the drawings.

Figure 1:
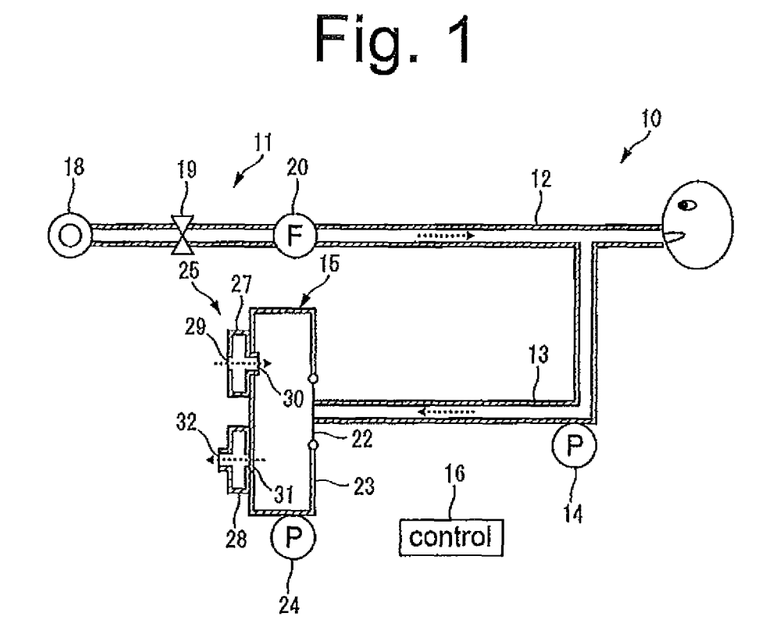
FIG. 1 is a schematic diagram illustrating a structure of a respiratory assistance device according to a first embodiment of the present invention.

In FIG. 1, a structure of a medical-use respiratory assistance device 10 according to a first embodiment of the present invention is illustrated. The respiratory assistance device 10 includes a supply source 11 of a gas that becomes inhaled air, an inhalation flow path 12 that guides the gas from the supply source 11 to a user, an exhalation flow path 13 that branches out from the inhalation flow path 12 and guides the exhaled air of the user to the outside air, an air pressure gauge 14 that measures the air pressure inside the exhalation flow path 13, an exhalation valve 15 that discharges the gas inside the exhalation flow path 13 to the outside air and adjusts the air pressure inside the exhalation flow path 13, and a control unit 16 that comprehensively controls the entire device.

The supply source 11 includes a gas tank 18 that stores a gas, such as air and oxygen, in a compressed state, an adjustment valve 19 that adjusts a flow rate of the gas supplied from the gas tank 18, and a flow meter 20 that measures the flow rate of the gas adjusted by the adjustment valve 19. The adjustment valve 19 is controlled on the basis of respective sensing data (measurement results, sensing signals) of the air pressure gauge 14 and the flow meter 20. The adjustment valve 19 is not limited to a specific type of valves, and an electric-operated valve, an electromagnetic valve having a fast response speed, etc. can be adopted. The flow meter 20 outputs the sensing data to the control unit 16.

The inhalation flow path 12 and the exhalation flow path 13 are each formed of a resin bellow-shaped tube and integrally constitute a single space. Air pressure inside the inhalation flow path 12 matches the air pressure inside the exhalation flow path 13 under a steady state. The exhalation valve 15 is provided at an outlet of the exhalation flow path 13 branching out from the inhalation flow path 12. The air pressure gauge 14 outputs the sensing data to the control unit 16.

The exhalation valve 15 functions as a check valve that discharges the exhaled air to the outside air. The exhalation valve 15 includes a diaphragm 22 that opens and closes the outlet of the exhalation flow path 13, a back chamber 23 that is provided on the opposite side of the exhalation flow path 13 with respect to the diaphragm 22 and forms a space together with the diaphragm 22, an air pressure gauge 24 that measures the air pressure inside the back chamber 23, and a pump unit 25 that is fixed directly to the circumference of the back chamber 23 and feeds and discharges air to and from the back chamber 23 to adjust the air pressure inside the back chamber 23.

The diaphragm 22 is a thin plate that is slightly larger than the outlet of the exhalation flow path 13 and arranged so as to block the outlet. More specifically, the diaphragm 22 is arranged so as to separate a space inside the exhalation flow path 13 from a space inside the back chamber 23. The diaphragm 22 functions using a difference in air pressures between the space inside the exhalation flow path 13 and the space inside the back chamber 23 and opens the exhalation flow path 13 by deforming in the direction moving farther away from the outlet.

Figure 2:
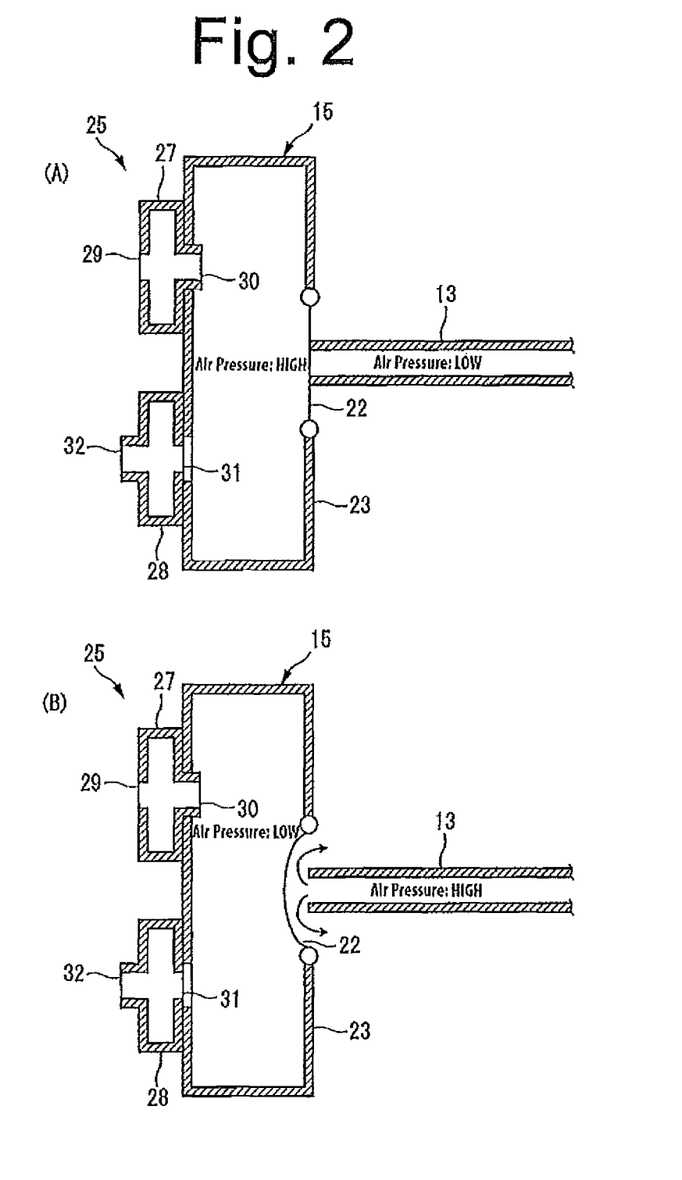
FIG. 2 includes cross-sectional views illustrating a control example of an exhalation valve with (A) illustrating a state in which an outlet of an exhalation flow path is closed and (B) illustrating a state in which the outlet of the exhalation flow path is opened.

More specifically, as shown in FIG. 2(A), when the air pressure of the exhalation flow path 13 is lower than the air pressure inside the back chamber 23, the diaphragm 22 adheres to and seals the outlet of the exhalation flow path 13. On the other hand, as shown in FIG. 2 (B), when the air pressure inside the exhalation flow path 13 is higher than the air pressure inside the back chamber 23, the diaphragm 22 deforms to the side of the back chamber 23 and opens the exhalation flow path 13, whereby the exhaled air is released to the outside air.

A description will be given while returning to FIG. 1. The air pressure gauge 24 outputs the sensing data to the control unit 16. The pump unit 25 includes an air feeding micro pump 27 that feeds air to the back chamber 23 and an air discharging micro pump 28 that discharges air from the back chamber 23. Note that, although a description is given using a case in which the pump unit 25 is directly fixed to the circumference of the back chamber 23 as an example in the present embodiment, it is sufficient that a pump unit of the present invention is provided on the circumference of a back chamber. The "circumference of a back chamber" used herein may include such a case in which the pump unit is provided at a distance from the back chamber while having a part or parts interposed therebetween. However, from a viewpoint of responsiveness, it is preferable that the pump unit be directly fixed to the circumference of the back chamber.

The air feeding micro pump 27 includes an air feeding inlet 29 that takes in a gas from outside the back chamber 23, an air feeding outlet 30 that is directly connected to the back chamber 23 and discharges the gas taken in from the air feeding inlet 29 to the back chamber 23, and the like. The air feeding micro pump 27 is controlled by the control unit 16 on the basis of the respective sensing data of the air pressure gauges 14 and 24.

The air discharging micro pump 28 includes an air discharging inlet 31 that is directly connected to the back chamber 23 and directly takes in the gas from inside the back chamber 23, an air discharging outlet 32 that discharges the gas taken in from the air discharging inlet 31 to outside the back chamber 23, and the like. The air discharging micro pump 28 is controlled by the control unit 16 on the basis of the respective sensing data of the air pressure gauges 14 and 24.

More specifically, the control unit 16 controls the pump unit 25 on the basis of the sensing data of the air pressure gauges 14 and 24 such that one of the air pressures inside the exhalation flow path 13 and inside the back chamber 23 becomes slightly higher than the other while maintaining a difference between the air pressures inside the exhalation flow path 13 and inside the back chamber 23 at substantially zero.

Note that "maintaining a difference at substantially zero" used herein means that the difference is close to zero to an extent that the diaphragm 22 can easily open while deforming to the side of the back chamber 23 and discharge a cough or a sneeze of the user from the outlet of the exhalation flow path 13, when the user coughs or sneezes, in a case when the diaphragm 22 is adhered to and sealing the outlet of the exhalation flow path 13 by slightly increasing the air pressure inside the back chamber 23. Further, in a case when the diaphragm 22 is opened while deforming to the side of the back chamber 23 by slightly increasing the air pressure inside the exhalation flow path 13, the "maintaining a difference at substantially zero" used herein means that the difference is close to zero to an extent that the diaphragm 22 can easily adhere to and seal the outlet of the exhalation flow path 13 when the user suddenly inhales.

Figure 3:
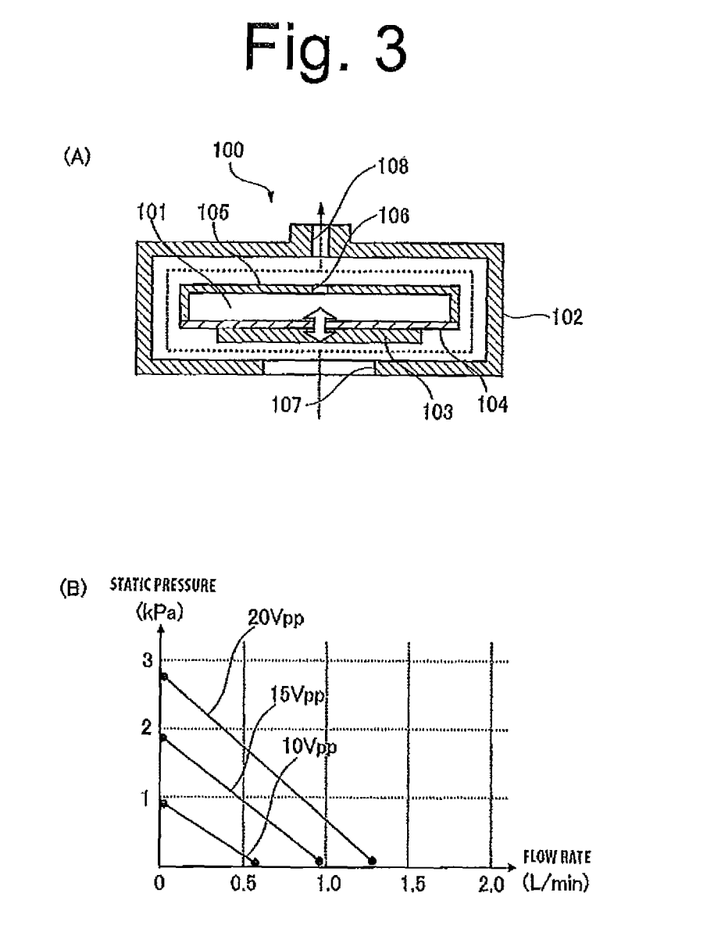

A micro pump 100 shown in FIG. 3(A) is adopted as each of the air feeding micro pump 27 and the air discharging micro pump 28. The micro pump 100 has been proposed in the Patent Literature WO2008/069266 and includes a primary blower chamber 101 and a secondary blower chamber 102 that is formed on an outer side of the primary blower chamber 101.

The primary blower chamber 101 includes a piezoelectric element 103 serving as a vibration source, a diaphragm 104 to which the piezoelectric element 103 is fixed, and a vibration frame 105 that forms a space together with the diaphragm 104. The vibration frame 105 has an opening 106 that moves a fluid inside and outside the primary blower chamber 101. The secondary blower chamber 102 has an inlet 107 on a side of the diaphragm 104 and also has an outlet 108 that is arranged so as to face the opening 106.

In the above-described micro pump 100, when the piezoelectric element 103 causes the diaphragm 104 to resonate, the fluid moves between the primary blower chamber 101 and the secondary blower chamber 102, and a resulting fluid resistance causes the vibration frame 105 to resonate. Due to the resonance between the diaphragm 104 and the vibration frame 105, the fluid is sucked from the inlet 107 and discharged through the outlet 108.

The micro pump 100 is suitable as a blower for transporting a gas and can transport the gas without using a check valve. Although the micro pump 100 is extremely small, being formed in a box-shape with an approximate external diameter of 20 mm×20 mm×2 mm, when an input sine wave is set at 26 kHz at 15 Vpp (Volt peak to peak), the micro pump 100 can transport air at a maximum rate of approximately 1 L/min (when static pressure is 0 Pa) and can also obtain approximately up to 2 kPa (flow rate is 0 L/min) static pressure.

On the other hand, since the micro pump 100 transports the fluid using the vibration of the diaphragm 104, which is caused by the piezoelectric element 103, there is naturally a limit to a volume of the fluid that can be transported, and static pressure/flow rate characteristics also show a line as shown in FIG. 3(B). More specifically, for example, when obtaining a static pressure of approximately 1 kPa, the flow rate becomes 0.5 L/min.

Note that, when the Vpp of the input sine wave is changed to 10, 20, or the like, since the amplitude of the piezoelectric element 103 changes, it is possible to change the flow rate and the pressure. More specifically, when the Vpp of the input sine wave is changed smoothly, it is possible to change the flow rate and the pressure smoothly. Further, when a frequency of the input sine wave is changed, it is possible to change the flow rate and the pressure. More specifically, when the frequency of the input sine wave is changed smoothly, it is possible to change the flow rate and the pressure smoothly. However, each of the flow rate and the pressure has an upper limit depending on the capacity of the piezoelectric element 103 and the strength and durability of the members. Normally, a rated Vpp and frequency are used.

Note that, although a monomorph (unimorph) structure is introduced in which one of the piezoelectric element 103 is attached to the diaphragm 104, it is of course possible to adopt a bimorph structure that increases an amount of vibration by attaching two piezoelectric elements together. Note that there are various other types for use as the micro pump 100, such as one including a structure suitable for transporting liquid. Therefore, in the present invention, an optimum structure may be adopted depending on the object thereof. More specifically, although the above-described micro pump 100 can transport the gas without using the check valve, a micro pump provided with check valves for an inlet and an outlet may be adopted instead of the micro pump 100.

Figure 4:
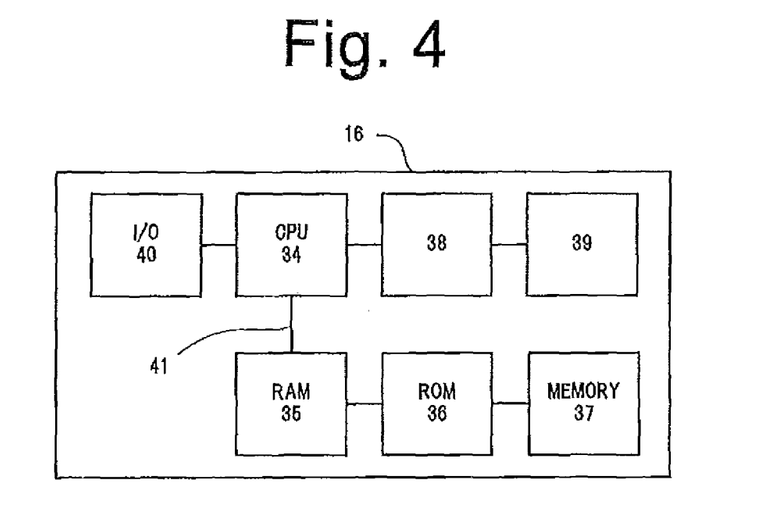
FIG. 4 is a block diagram showing a hardware structure of a control device used in the pump unit.

As shown in FIG. 4, as a hardware structure, the control unit 16 includes a CPU 34, a first storage medium 35, a second storage medium 36, a third storage medium 37, an input device 38, a display device 39, an input/output interface 40, and a bus 41.

The CPU 34 is a so-called central processing unit and causes various programs to be performed and realizes various functions of the control unit 16. The first storage medium 35 is a so-called RAM (Random Access Memory) and is used as a work area of the CPU 34. The second storage medium 36 is a so-called ROM (Read Only Memory) and stores a basic OS that is performed on the CPU 34. The third storage medium 37 is formed by a hard disk device that has a built-in magnetic disk, a disk device that houses a CD, a DVD, a BD, or the like, a volatile semiconductor flash memory device, etc. and saves the various programs performed in the CPU 34, the sensing data of the air pressure gauges 14 and 24 and the flow meter 20, and the like.

The input device 38 is an input key, a keyboard, a mouse or the like and inputs various information. The display device 39 is a display and displays various operational states. In the input/output interface 40, the sensing data of the air pressure gauges 14 and 24 and the flow meter 20, a power source (a sine wave shape) and a control signal for operating the air feeding micro pump 27 and the air discharging micro pump 28 are input and output. Further, the input/output interface 40 obtains data, such as programs, from an external personal computer and also outputs sensing data to the external personal computer. The bus 41 integrally connects the CPU 34, the first storage medium 35, the second storage medium 36, the third storage medium 37, the input device 38, the display device 39, the input/output interface 40, etc. and forms wiring for performing communication therebetween.

Figure 5:
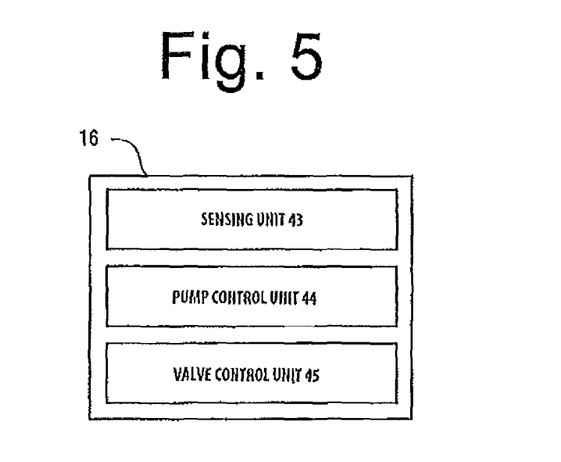
FIG. 5 is a block diagram showing a functional structure of the control device used in the pump unit.

In FIG. 5, a functional structure is shown that can be obtained as a result of a control program stored in the control unit 16 being performed by the CPU 34. The control unit 16 includes, as functional constituents, a sensing unit 43, a pump control unit 44, and a valve control unit 45. The sensing unit 43 constantly obtains the sensing data of the air pressure gauges 14 and 24 and transmits the data to the pump control unit 44. Further, the sensing unit 43 constantly obtains the sending data of the flow meter 20 and transmits the data to the valve control unit 45. The pump control unit 44 refers to the sensing data of the sensing unit 43 and controls the Vpp and the frequency of the input sine wave fed to the air feeding micro pump 27 and the air discharging micro pump 28 to cause values thereof to become closer to obtain target flow rate and pressure values. The valve control unit 45 refers to the sensing data of the sensing unit 43 and controls a control signal to the adjustment valve 19 to cause a value thereof to become closer to obtain the target flow rate value.

Next, a control example of the respiratory assistance device 10 will be described.

Figure 6:
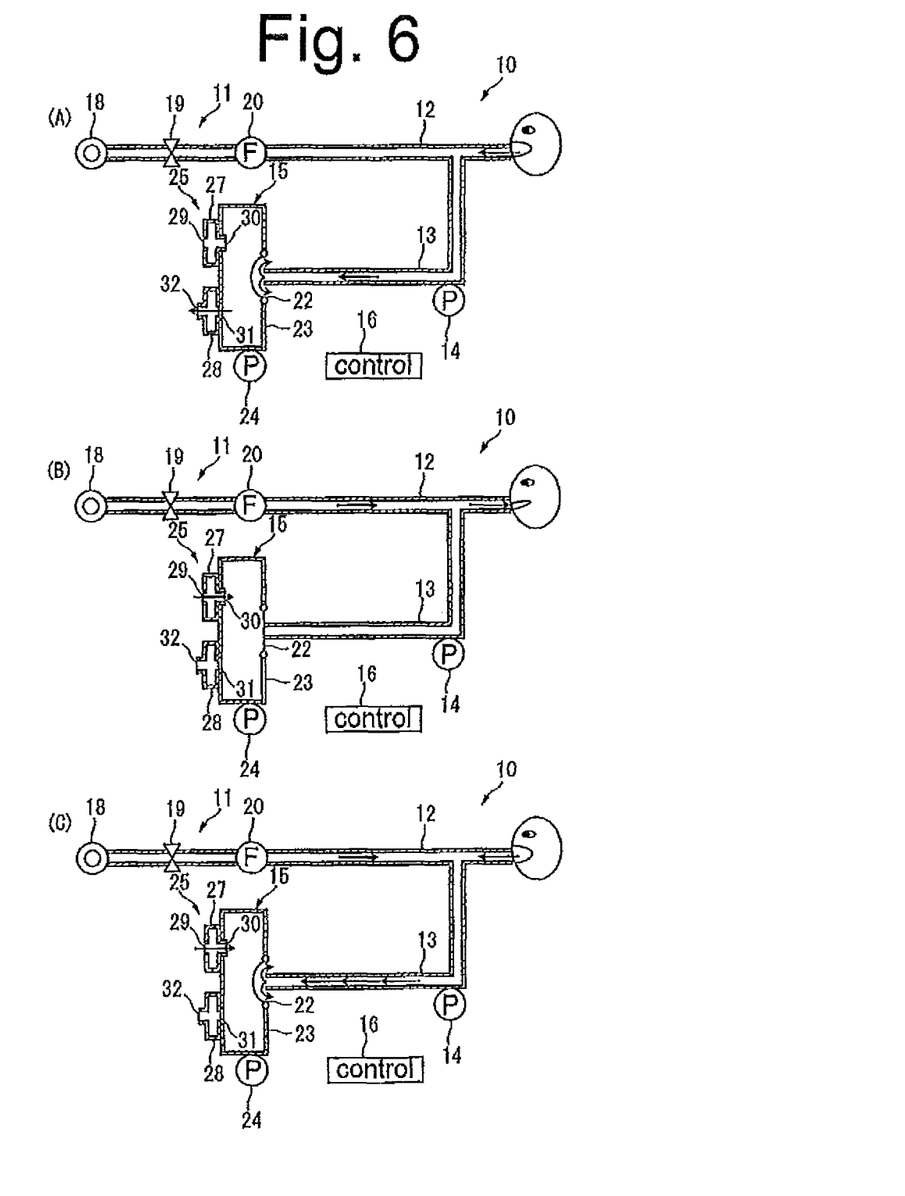
FIG. 6 includes schematic diagrams illustrating a control example of the respiratory assistance device with (A) illustrating a case in which a user exhales, (B) illustrating a case in which the user inhales, and (C) illustrating a case in which the user coughs or sneezes at a time of exhaling.

As shown in FIG. 6 (A), when the user exhales, the pressure inside the exhalation flow path 13 increases. When the pressure inside the exhalation flow path 13 increases, the increased pressure is sensed by the air pressure gauge 14. The sensing data are output to the control unit 16. The control unit 16 controls the pump unit 25 based on the sensing data. More specifically, the air discharging micro pump 28 is operated to discharge air from the back chamber 23, whereby the pressure inside the back chamber 23 decreases. As a result, the air pressure inside the exhalation flow path 13 becomes higher than the air pressure inside the back chamber 23, and the diaphragm 22 opens the exhalation flow path 13 by deforming in the direction moving farther away from the outlet. The exhaled air is released from the exhalation flow path 13.

As a result of the release of the exhaled air, the pressure inside the exhalation flow path 13 decreases. When the pressure inside the exhalation flow path 13 decreases, the decreased pressure is sensed by the air pressure gauge 14. The sensing data are output to the control unit 16. The control unit 16 controls the pump unit 25 on the basis of the sensing data. More specifically, the air discharging micro pump 28 is stopped. Then, a state in which the air pressure inside the exhalation flow path 13 is higher than the air pressure inside the back chamber 23 is released, the deformation of the diaphragm 22 is also released, and the exhalation flow path 13 is sealed.

Next, as shown in FIG. 6(B), when the user inhales, the pressure inside the exhalation flow path 13 decreases. When the pressure inside the exhalation flow path 13 decreases, the decreased pressure is sensed by the air pressure gauge 14. The sensing data are output to the control unit 16. The control unit 16 controls the pump unit 25 and the supply source 11 on the basis of the sensing data. More specifically, the air feeding micro pump 27 is operated to feed air to the back chamber 23, so that the pressure inside the back chamber 23 increases. As a result, the air pressure inside the exhalation flow path 13 becomes lower than the air pressure inside the back chamber 23, and the diaphragm 22 tightly seals the exhalation flow path 13. Further, in accordance with the operation of the air feeding micro pump 27, the adjustment valve 19 is opened, so that the gas is supplied from the gas tank 18.

Next, as shown in FIG. 6(C), when the user coughs or sneezes, the pressure inside the exhalation flow path 13 abruptly increases. As a result, the air pressure inside the exhalation flow path 13 becomes higher than the air pressure inside the back chamber 23, and the diaphragm 22 opens the exhalation flow path 13 by deforming in the direction moving further away from the outlet. The cough or sneeze is released from the outlet of the exhalation flow path 13.

According to the above-described respiratory assistance device 10, since the pump unit 25 is fixed to the circumference of the back chamber 23, the exhalation valve can be accurately controlled without requiring much response time for power from the pump unit 25 to act on the back chamber 23. As a result, no trouble is caused in medical practice in which human lives are at stake. Further, since the back chamber 23 and the pump unit 25 are integrally provided, even when the back chamber 23 moves in conjunction with body movements of the user, this does not cause a connection between the back chamber 23 and the pump unit 25 to be cut off as the back chamber 23 and the pump unit 25 move together. Therefore, the safety of a respiratory assistance operation is improved, and at the same time, it becomes easier for the user to move his/her body.

Furthermore, since the pump unit 25 includes each of the air feeding micro pump 27 and the air discharging micro pump 28, switching control of feeding and discharging air to and from the back chamber 23 is accurately performed. Further, since each of the micro pumps 27 and 28 is small, even if a plurality of pump units are arranged, they can be configured in a smaller and lighter manner than a conventional pump unit, such as a blower. In addition, since the miniaturized pump unit 25 is directly fixed to the back chamber 23, the respiratory assistance device 10 can be configured in an extremely compact manner.

Figure 7:
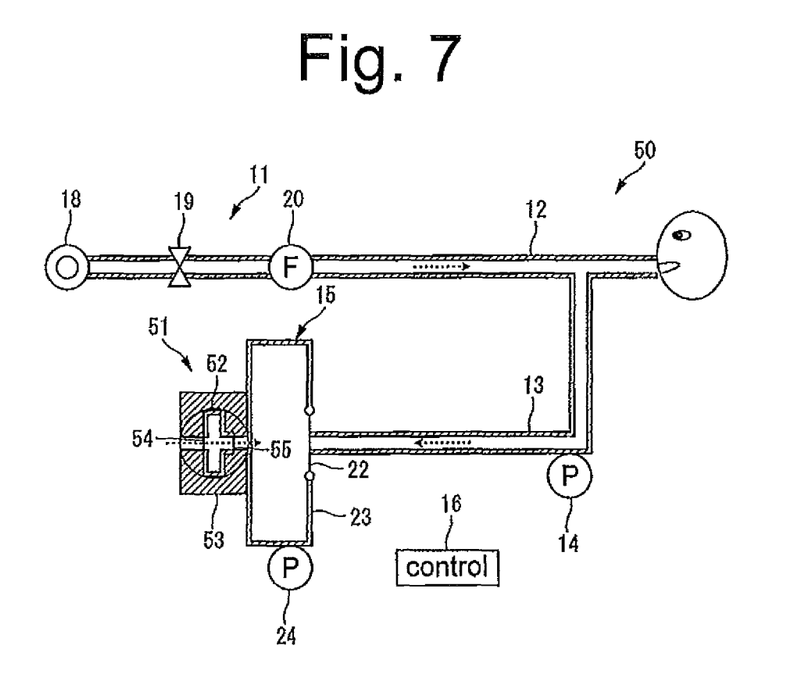
FIG. 7 is a schematic diagram illustrating a structure of a respiratory assistance device according to a second embodiment of the present invention.

In FIG. 7, a structure of a medical-use respiratory assistance device 50 according to a second embodiment is illustrated. Note that, since the first embodiment and the second embodiment share the same and similar portions, descriptions for those will be omitted and points that are different from the first embodiment will be mainly described below. Also, with respect to a third embodiment that will be described below, common descriptions with other embodiments will be omitted and points that are different from the other embodiments will be mainly described.

The respiratory assistance device 50 includes a pump unit 51 that adopts one micro pump 52 instead of the pump unit 25 that adopts the two micro pumps 27 and 28. The pump unit 51 includes the micro pump 52 that selectively performs the feeding and discharging of the air to and from the back chamber 23 and a switching mechanism 53 that causes the feeding and discharging of the air to and from the back chamber 23 to be performed selectively by switching the position of the micro pump 52.

The micro pump 52 includes an inlet 54 that takes in a gas, and an outlet 55 that discharges the gas taken in from the inlet 54, etc. The micro pump 52 adopts the micro pump 100 shown in FIG. 3(A).

Figure 8:
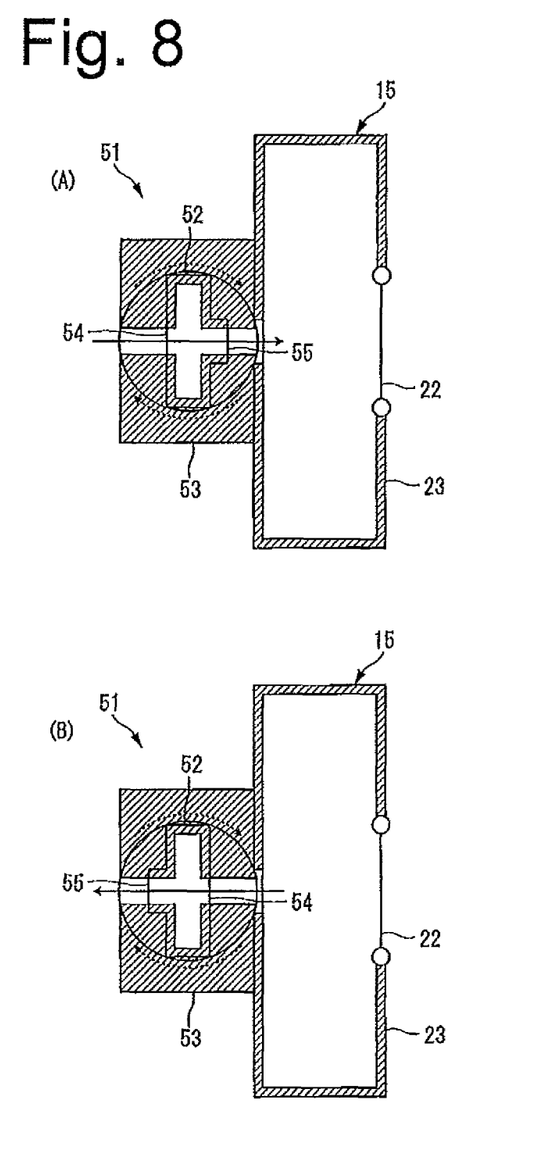
FIG. 8 includes schematic diagrams illustrating a control example of the pump unit with (A) illustrating a state in which a position of the micro pump becomes an air feeding position for feeding air to a back chamber and (B) illustrating a state in which the position of the micro pump becomes an air discharging position for discharging air from the back chamber.

The position of the micro pump 52 is switched by the switching mechanism 53 to cause connection relationships of the inlet 54 and the outlet 55 with the back chamber 23 to be switched, whereby one of the inlet 54 and the outlet 55 is selectively connected to the back chamber 23. More specifically, the position of the micro pump 52 is switched between an air feeding position shown in FIG. 8(A) and an air discharging position shown in FIG. 8(B). In the air feeding position, the outlet 55 is directly connected to the back chamber 23, and the micro pump 52 feeds air to the back chamber 23. In the air discharging position, the inlet 54 is directly connected to the back chamber 23, and the micro pump 52 discharges air from the back chamber 23.

Figure 9:
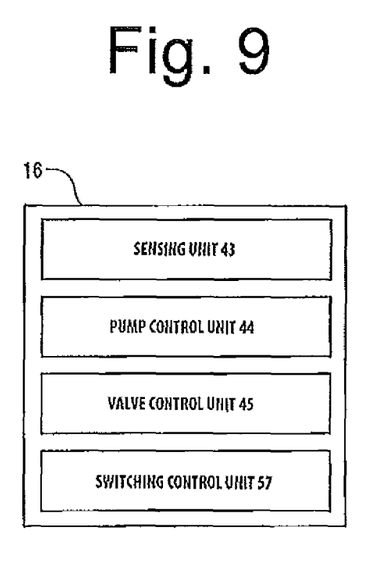
FIG. 9 is a block diagram illustrating a functional structure of the control device used in the pump unit.

In FIG. 9, a functional structure is shown that is obtained by the control program stored in the control unit 16 being performed by the CPU 34. The control unit 16 includes a switching control unit 57 and the like as a functional structure. The sensing unit 43 constantly obtains the sensing data of the air pressure gauges 14 and 24 and transmits the data to the switching control unit 57. The switching control unit 57 refers to the sensing data of the sensing unit 43 and controls a control signal to the switching mechanism 53 to cause the micro pump 52 to be in a target position.

Next, a control example of the respiratory assistance device 50 will be described.

Figure 10:
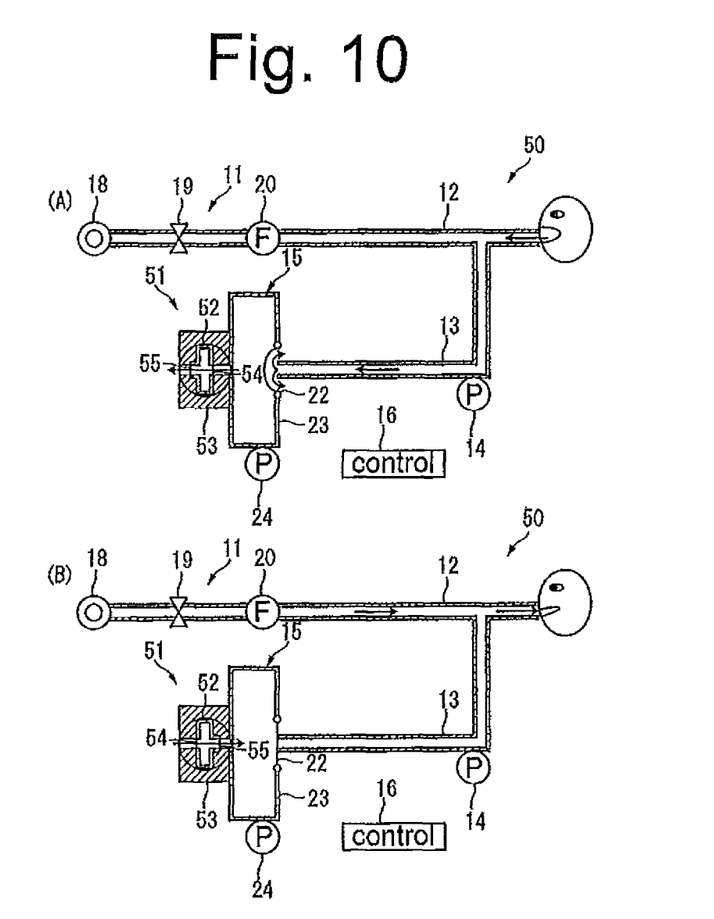
FIG. 10 includes schematic diagrams showing a control example of the respiratory assistance device with (A) illustrating a case in which the user exhales and (B) illustrating a case in which the user inhales.

As shown in FIG. 10(A), when the user exhales, the pressure inside the exhalation flow path 13 increases. When the pressure inside the exhalation flow path 13 increases, the increased pressure is sensed by the air pressure gauge 14. The sensing data are output to the control unit 16. The control unit 16 controls the pump unit 51 on the basis of the sensing data. More specifically, the switching mechanism 53 is operated to switch the position of the micro pump 52 to the air discharging position, and at the same time, the micro pump 52 is operated to discharge air from the back chamber 23 to cause the pressure inside the back chamber 23 to decrease. As a result, the air pressure inside the exhalation flow path 13 becomes higher than the air pressure inside the back chamber 23, and the diaphragm 22 opens the exhalation flow path 13 by deforming in the direction moving farther away from the outlet. The exhaled air is released from the outlet of the exhalation flow path 13. After that, until the user inhales, the control unit 16 performs control in the same manner as described with respect to the respiratory assistance device 10 of the first embodiment.

Next, as shown in FIG. 10 (B), when the user inhales, the pressure inside the exhalation flow path 13 decreases. When the pressure inside the exhalation flow path 13 decreases, the decreased pressure is sensed by the air pressure gauge 14. The sensing data are output to the control unit 16. The control unit 16 controls the pump unit 51 and the supply source 11 on the basis of the sensing data. More specifically, the switching mechanism 53 is operated to switch the position of the micro pump 52 to the air feeding position, and at the same time, the micro pump 52 is operated to feed air to the back chamber 23 to cause the pressure inside the back chamber 23 to increase. As a result, the air pressure inside the exhalation flow path 13 becomes lower than the air pressure inside the back chamber 23, and the diaphragm 22 tightly seals the exhalation flow path 13. Further, in accordance with an operation of the micro pump 52, the adjustment valve 19 is opened and the gas is supplied from the gas tank 18.

According to the above-described respiratory assistance device 50, the feeding and discharging of the air to and from the back chamber 23 can be performed while providing the single micro pump 52. As a result, the respiratory assistance device 50 can be configured in an even smaller and lighter manner than the respiratory assistance device 10 of the first embodiment.

Figure 11:
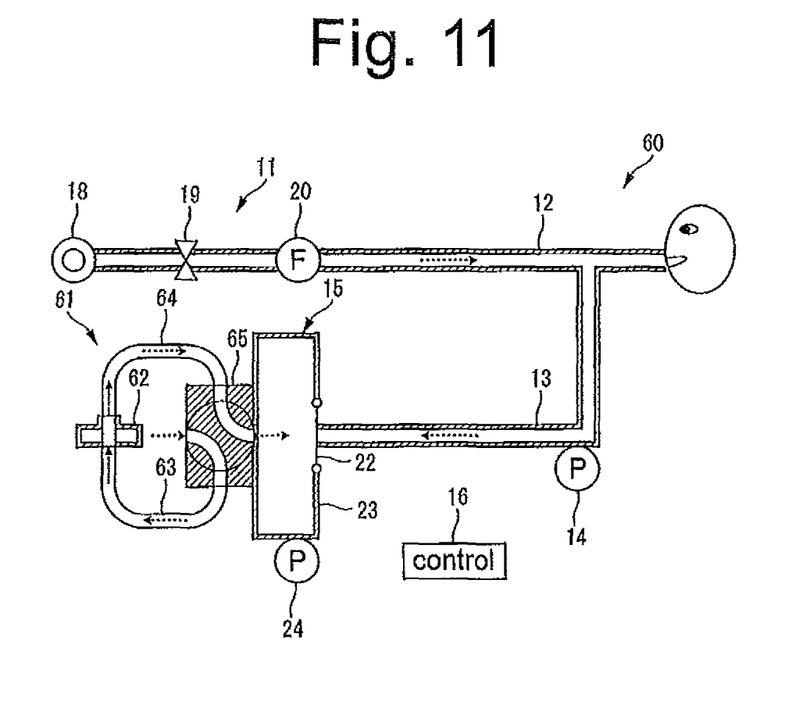
FIG. 11 is a schematic diagram illustrating a structure of a respiratory assistance device according to a third embodiment of the present invention.

In FIG. 11, a structure of a medical-use respiratory assistance device 60 according to a third embodiment is illustrated. The respiratory assistance device 60 includes a pump unit 61 that switches connection relationships without changing positions of a micro pump 62, instead of the pump unit 51 that switches the connection relationships by changing the positions of the micro pump 52. The pump unit 61 includes the micro pump 62 that selectively performs the feeding and discharging of the air to and from the back chamber 23, an inlet pipe 63 to which an inlet of the micro pump 62 is connected, an outlet pipe 64 to which an outlet of the micro pump is connected, and a switching valve 65 that switches connection relationships of the inlet pipe 63 and the outlet pipe 64 with the back chamber 23.

The micro pump 62 includes an inlet, an outlet (for both of which reference numerals are omitted), etc. The micro pump 100 shown in FIG. 3(A) is adopted as the micro pump 62.

Figure 12:
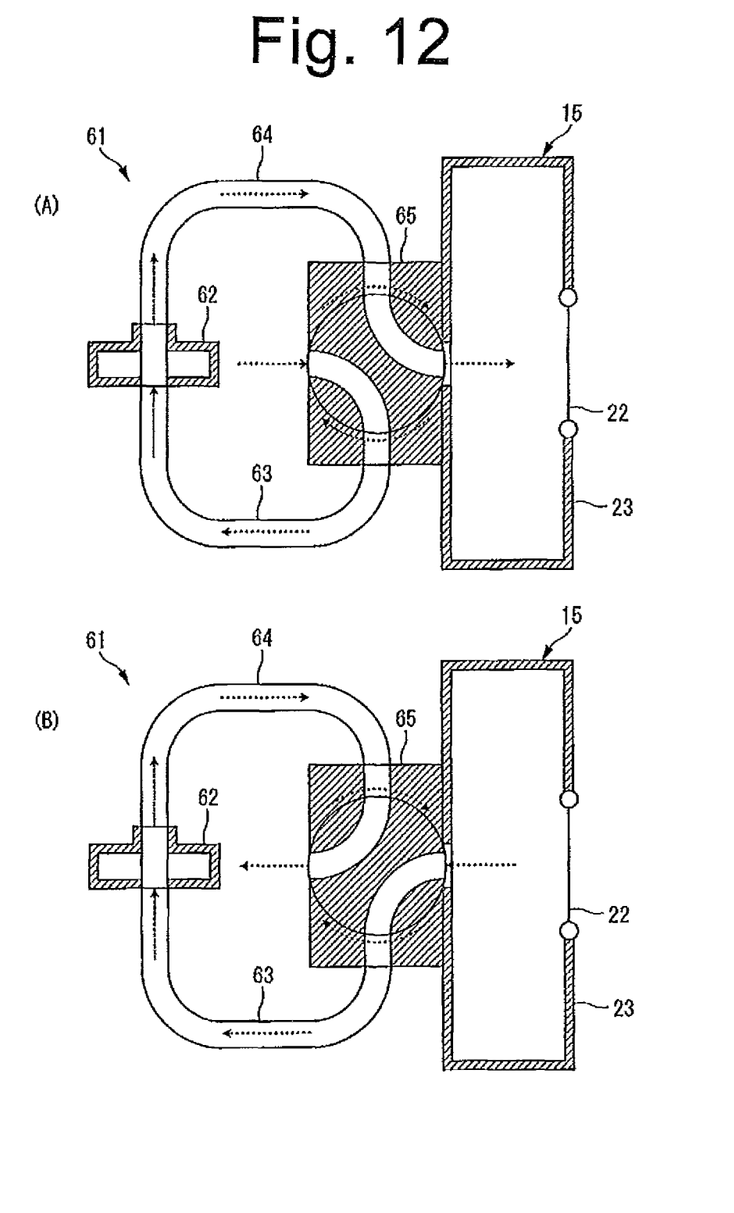
FIG. 12 includes schematic diagrams illustrating a control example of the pump unit with (A) illustrating a state in which the position of the micro pump becomes the air feeding position for feeding air to the back chamber and (B) illustrating a state in which the position of the micro pump becomes the air discharging position for discharging air from the back chamber.

In the micro pump 62, the connection relationships of the inlet and the outlet with the back chamber 23 are switched by the switching valve 65, and one of the inlet and the outlet is selectively connected to the back chamber 23. More specifically, the connection relationships are switched between an air feeding state shown in FIG. 12(A) and an air discharging state shown in FIG. 12(B). In the air feeding state, the outlet pipe 64 is directly connected to the back chamber 23, and the micro pump 62 feeds air to the back chamber 23, the air discharging state, the inlet pipe 63 is directly connected to the back chamber 23, and the micro pump 62 discharges air from the back chamber 23.

Note that the pump unit and the respiratory assistance device of the present invention are not limited to the above-described embodiments, and various modifications can, of course, be made, without departing from the spirit and scope of the present invention. Further, constituent elements of the above-described embodiments may be applied to other embodiments to a possible extent.

More specifically, although one air feeding micro pump 27 and one air discharging micro pump 28 are provided in the respiratory assistance device 10 of the first embodiment, the numbers of the respective pumps may be plural. In this case, the plurality of micro pumps may be connected in series, in parallel, or in a grid pattern forming a relationship of rows and columns (in series and parallel). Further, the number and the arrangement of the air feeding micro pump 27 and the number and the arrangement of the air discharging micro pump 28 may be different from each other. In these cases, even if an individual micro pump breaks down, other micro pumps compensate for the broken micro pump, so that it also becomes possible to improve safety.

Further, although the control unit 16 operates one of the air feeding micro pump 27 and the air discharging micro pump 28 in the respiratory assistance device 10 of the first embodiment, the present invention is not limited to that control mode. More specifically, the control unit 16 may cause both of the air feeding micro pump 27 and the air discharging micro pump 28 to operate and control the air pressure of the back chamber 23 by stopping the operation of one of the air feeding micro pump 27 and the air discharging micro pump 28. As a result, it is possible to eliminate a time lag due to a delay in starting up and to control the exhalation valve 15 even more accurately.

Further, although the feeding and discharging of the air to and from the back chamber 23 are switched by the switching mechanism 53 switching the position of the micro pump 52 in the respiratory assistance device 50 according to the second embodiment, the feeding and discharging of the air to and from the back chamber 23 may be switched by switching pathways of the micro pump 52 using an electromagnetic valve, etc. while keeping the position of the micro pump 52 unchanged.

Further, in the respiratory assistance devices 50 and 60 according to the second and third embodiments, the number of the micro pump 52 and the number of the micro pump 62 are not limited to one and may be plural. In this case, the micro pumps may be connected in series, in parallel, or in a grid pattern forming a relationship of rows and columns (in series and parallel).

INDUSTRIAL APPLICABILITY

A respiratory assistance device of the present invention can be used for the purpose of respiratory assistance of various living organisms.

REFERENCE SIGNS LIST 10, 50, 60 Respiratory assistance device
11 Supply source
12 Inhalation flow path
13 Exhalation flow path
14, 24 Air pressure gauge
15 Exhalation valve
16 Control unit
22 Diaphragm
23 Back chamber
25, 51, 61 Pump unit
27 Air feeding micro pump
28 Air discharging micro pump
29 Air feeding inlet
30 Air feeding outlet
31 Air discharging inlet
32 Air discharging outlet
52, 62, 100 Micro pump
53 Switching mechanism
54, 107 Inlet
55, 108 Outlet

The invention claimed is:

1. An exhalation valve comprising:
a diaphragm for opening and closing an outlet of an exhalation flow path for guiding exhaled air to outside air;
a back chamber that is provided on an opposite side of the diaphragm from the exhalation flow path and forms a space together with the diaphragm;
a micro-pump system comprising a feeding micro-pump and a discharging micro-pump, the feeding micro-pump and the discharging micro-pump of the micro-pump system being directly located at and directly set to the back chamber, the micro-pump system adjusting an air pressure inside the back chamber by feeding air directly from the feeding micro-pump to the back chamber and by discharging air directly from the back chamber to the discharging micro-pump; and
a control unit for controlling an operation of the micro-pump system;
wherein the control unit simultaneously operates both the feeding micro-pump and the discharging micro-pump and then stops one of the feeding micro-pump and the discharging micro-pump from operating to control the air pressure inside the back chamber; and
wherein the diaphragm uses a difference between an air pressure inside the exhalation flow path and the air pressure inside the back chamber to close the outlet when the air pressure inside the exhalation flow path is lower than the air pressure inside the back chamber, and to open the outlet when the air pressure inside the exhalation flow path is higher than the air pressure inside the back chamber.

2. The exhalation valve according to claim 1, comprising:
a first air pressure gauge for measuring the air pressure inside the exhalation flow path to output a measurement result to the control unit, and
a second air pressure gauge for measuring the air pressure inside the back chamber to output a measurement result to the control unit, and wherein the control unit controls the operation of the micro-pump system on the basis of the measurement results of the first and second air pressure gauges to cause the difference between the air pressure inside the exhalation flow path and the air pressure inside the back chamber to become substantially zero.

3. The exhalation valve according to claim 1, wherein the feeding micro-pump includes an air feeding inlet that takes in a gas from outside the back chamber and an air feeding outlet that is directly connected to the back chamber and discharges the gas taken in from the air feeding inlet into the back chamber, and
the discharging micro-pump includes an air discharging inlet that is directly connected to the back chamber and directly takes in the gas from inside the back chamber and an air discharging outlet that discharges the gas taken in from the air discharging inlet to outside the back chamber.

4. A respiratory assistance device comprising:
an exhalation valve including:
 a diaphragm for opening and closing an outlet of an exhalation flow path for guiding exhaled air to outside air;
 a back chamber that is provided on an opposite side of the diaphragm from the exhalation flow path and forms a space together with the diaphragm;
 a micro-pump system comprising a feeding micro-pump and a discharging micro-pump, the feeding micro-pump and the discharging micro-pump of the micro-pump system being directly located at and directly set to the back chamber, the micro-pump system adjusting an air pressure inside the back chamber by feeding air directly from the feeding micro-pump to the back chamber and by discharging of air directly from the back chamber to the discharging micro-pump; and
 a control unit for controlling an operation of the micro-pump system;
 wherein the control unit simultaneously operates both the feeding micro-pump and the discharging micro-pump and then stops one of the feeding micro-pump and the discharging micro-pump from operating to control the air pressure inside the back chamber; and
 wherein the diaphragm uses a difference between an air pressure inside the exhalation flow path and the air pressure inside the back chamber to close the outlet when the air pressure inside the exhalation flow path is lower than the air pressure inside the back chamber, and to open the outlet when the air pressure inside the exhalation flow path is higher than the air pressure inside the back chamber;
an inhalation flow path for guiding a gas from a supply source, which is different from the micro-pump system, to a living organism, the gas becoming exhaled air; and
the exhalation flow path for guiding the exhaled air of the living organism to outside air; and wherein
the exhalation valve adjusts the air pressure inside the exhalation flow path by releasing the gas inside the exhalation flow path to the outside air.

\* \* \* \* \*